United States Patent
Garrison

(10) Patent No.: US 9,011,436 B2
(45) Date of Patent: Apr. 21, 2015

(54) DOUBLE-LENGTH JAW SYSTEM FOR ELECTROSURGICAL INSTRUMENT

(71) Applicant: Covidien LP, Mansfield, MA (US)

(72) Inventor: David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 13/834,703

(22) Filed: Mar. 15, 2013

(65) Prior Publication Data

US 2013/0345706 A1 Dec. 26, 2013

Related U.S. Application Data

(60) Provisional application No. 61/664,492, filed on Jun. 26, 2012.

(51) Int. Cl.
*A61B 18/18* (2006.01)
*A61B 18/14* (2006.01)
*A61B 18/00* (2006.01)

(52) U.S. Cl.
CPC .......... *A61B 18/1447* (2013.01); *A61B 18/1445* (2013.01); *A61B 2018/0063* (2013.01)

(58) Field of Classification Search
CPC ........... A61B 18/1445; A61B 18/1447; A61B 2018/0063; A61B 2018/1467
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003. cited by applicant.

(Continued)

*Primary Examiner* — George Manuel

(57) ABSTRACT

An electrosurgical forceps includes a handle having a shaft extending therefrom defining a longitudinal axis. The handle is selectively movable to translate movement of the shaft along the longitudinal axis to actuate a pair of laterally spaced first and second jaw members pivotably connected to a distal end of the shaft. The first and second jaw members are moveable from an open position, wherein the first and second jaw members are in spaced relation relative to a stationary jaw member, to a closed position wherein the first and second jaw members cooperate with the stationary jaw member to grasp tissue therebetween. Each of the jaw members is adapted to connect to an electrosurgical energy source to conduct energy through tissue grasped therebetween to effect a tissue seal.

20 Claims, 4 Drawing Sheets

(56) References Cited

U.S. PATENT DOCUMENTS

| | | | |
|---|---|---|---|
| D358,887 S | 5/1995 | Feinberg | |
| D384,413 S | 9/1997 | Zlock et al. | |
| 5,702,390 A * | 12/1997 | Austin et al. | 606/48 |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| 6,905,497 B2 | 6/2005 | Truckai et al. | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| 8,317,787 B2 | 11/2012 | Hanna | |
| 8,444,642 B2 | 5/2013 | Contijoch et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/040483 A1 | 4/2008 |
| WO | 2011/018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003. cited by applicant.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447. cited by applicant.

(56) References Cited

OTHER PUBLICATIONS

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. cited by applicant.
Peterson et al. "Comparison of Healing Process Following Ligation with Sutures and Bipolar Vessel Sealing" Surgical Technology International (2001). cited by applicant.
"Electrosurgery: A Historical Overview" Innovations in Electrosurgery; Sales/Product Literature; Dec. 31, 2000. cited by applicant.
Johnson et al. "Evaluation of a Bipolar Electrothermal Vessel Sealing Device in Hemorrhoidectomy" Sales/Product Literature; Jan. 2004. cited by applicant.
E. David Crawford "Evaluation of a New Vessel Sealing Device in Urologic Cancer Surgery" Sales/Product Literature 2000. cited by applicant.
Johnson et al. "Evaluation of the LigaSure Vessel Sealing System in Hemorrhoidectormy" American College of Surgeons (ACS) Clinicla Congress Poster (2000). cited by applicant.
Muller et al., "Extended Left Hemicolectomy Using the LigaSure Vessel Sealing System" Innovations That Work, Sep. 1999. cited by applicant.
Kennedy et al. "High-burst-strength, feedback-controlled bipolar vessel sealing" Surgical Endoscopy (1998) 12: 876-878. cited by applicant.
Burdette et al. "In Vivo Probe Measurement Technique for Determining Dielectric Properties At VHF Through Microwave Frequencies", IEEE Transactions on Microwave Theory and Techniques, vol. Mtt-28, No. 4, Apr. 1980 pp. 414-427. cited by applicant.
Carus et al., "Initial Experience With the LigaSure Vessel Sealing System in Abdominal Surgery" Innovations That Work, Jun. 2002. cited by applicant.
Heniford et al. "Initial Research and Clinical Results with an Electrothermal Bipolar Vessel Sealer" Oct. 1999. cited by applicant.
Heniford et al. "Initial Results with an Electrothermal Bipolar Vessel Sealer" Surgical Endoscopy (2000) 15:799-801. cited by applicant.
Herman et al., "Laparoscopic Intestinal Resection With the LigaSure Vessel Sealing System: A Case Report"; Innovations That Work, Feb. 2002. cited by applicant.
Koyle et al., "Laparoscopic Palomo Varicocele Ligation in Children and Adolescents" Pediatric Endosurgery & Innovative Techniques, vol. 6, No. 1, 2002. cited by applicant.
W. Scott Helton, "LigaSure Vessel Sealing System: Revolutionary Hemostasis Product for General Surgery"; Sales/Product Literature 1999. cited by applicant.
LigaSure Vessel Sealing System, the Seal of Confidence in General, Gynecologic, Urologic, and Laparaoscopic Surgery; Sales/Product Literature; Apr. 2002. cited by applicant.
Joseph Ortenberg "LigaSure System Used in Laparoscopic 1st and 2nd Stage Orchiopexy" Innovations That Work, Nov. 2002. cited by applicant.
Sigel et al. "The Mechanism of Blood Vessel Closure by High Frequency Electrocoagulation" Surgery Gynecology & Obstetrics, Oct. 1965 pp. 823-831. cited by applicant.
Sampayan et al, "Multilayer Ultra-High Gradient Insulator Technology" Discharges and Electrical Insulation in Vacuum, 1998. Netherlands Aug. 17-21, 1998; vol. 2, pp. 740-743. cited by applicant.
Paul G. Horgan, "A Novel Technique for Parenchymal Division During Hepatectomy" The American Journal of Surgery, vol. 181, No. 3, Apr. 2001 pp. 236-237. cited by applicant.
Benaron et al., "Optical Time-Of-Flight and Absorbance Imaging of Biologic Media", Science, American Association for the Advancement of Science, Washington, DC, vol. 259, Mar. 5, 1993, pp. 1463-1466. cited by applicant.
Olsson et al. "Radical Cystectomy in Females" Current Surgical Techniques in Urology, vol. 14, Issue 3, 2001. cited by applicant.

Palazzo et al. "Randomized clinical trial of Ligasure versus open haemorrhoidectomy" British Journal of Surgery 2002, 89, 154-157. cited by applicant.
Levy et al. "Randomized Trial of Suture Versus Electrosurgical Bipolar Vessel Sealing in Vaginal hysterectomy" Obstetrics & Gynecology, vol. 102, No. 1, Jul. 2003. cited by applicant.
"Reducing Needlestick Injuries in the Operating Room" Sales/Product Literature 2001. cited by applicant.
Bergdahl et al. "Studies on Coagulation and the Development of an Automatic Computerized Bipolar Coagulator" J. Neurosurg, vol. 75, July 1991, pp. 148-151. cited by applicant.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. cited by applicant.
Sayfan et al. "Sutureless Closed Hemorrhoidectomy: A New Technique" Annals of Surgery vol. 234 No. 1 Jul. 2001; pp. 21-24. cited by applicant.
Levy et al., "Update on Hysterectomy—New Technologies and Techniques" OBG Management, Feb. 2003. cited by applicant.
Dulemba et al. "Use of a Bipolar Electrothermal Vessel Sealer in Laparoscopically Assisted Vaginal Hysterectomy" Sales/Product Literature; Jan. 2004. cited by applicant.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574. cited by applicant.
Sengupta et al., "Use of a Computer-Controlled Bipolar Diathermy System in Radical Prostatectomies and Other Open Urological Surgery" ANZ Journal of Surgery (2001) 71.9 pp. 538-540. cited by applicant.
Rothenberg et al. "Use of the LigaSure Vessel Sealing System in Minimally Invasive Surgery in Children" Int'l Pediatric Endosurgery Group (IPEG) 2000. cited by applicant.
Crawford et al. "Use of the LigaSure Vessel Sealing System in Urologic Cancer Surgery" Grand Rounds in Urology 1999 vol. 1 Issue 4 pp. 10-17. cited by applicant.
Craig Johnson, "Use of the LigaSure Vessel Sealing System in Bloodless Hemorrhoidectomy" Innovations That Work, Mar. 2000. cited by applicant.
Levy et al. "Use of a New Energy-based Vessel Ligation Device During Vaginal Hysterectomy" Int'l Federation of Gynecology and Obstetrics (FIGO) World Congress, 1999. cited by applicant.
Barbara Levy, "Use of a New Vessel Ligation Device During Vaginal Hysterectomy" FIGO 2000, Washington, D.C. cited by applicant.
E. David Crawford "Use of a Novel Vessel Sealing Technology in Management of the Dorsal Veinous Complex" Sales/Product Literature 2000. cited by applicant.
Jarrett et al., "Use of the LigaSure Vessel Sealing System for Peri-Hilar Vessels in Laparoscopic Nephrectomy" Sales/Product Literature 2000. cited by applicant.
Crouch et al. "A Velocity-Dependent Model for Needle Insertion in Soft Tissue" MICCAI 2005; LNCS 3750 pp. 624-632, Dated: 2005. cited by applicant.
McLellan et al. "Vessel Sealing for Hemostasis During Pelvic Surgery" Int'l Federation of Gynecology and Obstetrics FIGO World Congress 2000, Washington, D.C. cited by applicant.
McLellan et al. "Vessel Sealing for Hemostasis During Gynecologic Surgery" Sales/Product Literature 1999. cited by applicant.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Schmaltz et al.
U.S. Appl. No. 09/591,328, filed Jun. 9, 2000, Ryan et al.
U.S. Appl. No. 12/336,970, filed Dec. 17, 2008, Sremcich et al.
U.S. Appl. No. 13/731,674, filed Dec. 31, 2012, Siebrecht.
U.S. Appl. No. 14/019,031, filed Sep. 5, 2013, Garrison.
U.S. Appl. No. 14/019,094, filed Sep. 5, 2013, Garrison.
U.S. Appl. No. 14/032,486, filed Sep. 20, 2013, Kendrick.
U.S. Appl. No. 14/035,423, filed Sep. 24, 2013, Garrison.
U.S. Appl. No. 14/037,772, filed Sep. 26, 2013, Frushour.
U.S. Appl. No. 14/041,995, filed Sep. 30, 2013, Kendrick.
U.S. Appl. No. 14/042,947, filed Oct. 1, 2013, Kendrick.
U.S. Appl. No. 14/043,039, filed Oct. 1, 2013, Rusin.

(56) References Cited

OTHER PUBLICATIONS

U.S. Appl. No. 14/043,322, filed Oct. 1, 2013, O'Neill.
U.S. Appl. No. 14/047,474, filed Oct. 7, 2013, Mueller.
U.S. Appl. No. 14/050,593, filed Oct. 10, 2013, Plaven.
U.S. Appl. No. 14/052,827, filed Oct. 14, 2013, Nau.
U.S. Appl. No. 14/052,856, filed Oct. 14, 2013, Latimer.
U.S. Appl. No. 14/052,871, filed Oct. 14, 2013, Kappus.
U.S. Appl. No. 14/054,173, filed Oct. 15, 2013, Payne.
U.S. Appl. No. 14/054,573, filed Oct. 15, 2013, Harper.
U.S. Appl. No. 14/064,310, filed Oct. 28, 2013, Reschke.
U.S. Appl. No. 14/065,644, filed Oct. 29, 2013, Reschke.
U.S. Appl. No. 14/080,564, filed Nov. 14, 2013, Lawes.
U.S. Appl. No. 14/080,581, filed Nov. 14, 2013, Kerr.
U.S. Appl. No. 14/083,696, filed Nov. 19, 2013, Horner.
U.S. Appl. No. 14/086,399, filed Nov. 21, 2013, Allen.
U.S. Appl. No. 14/091,505, filed Nov. 27, 2013, Garrison.
U.S. Appl. No. 14/091,521, filed Nov. 27, 2013, Garrison.
U.S. Appl. No. 14/091,532, filed Nov. 27, 2013, Garrison.
U.S. Appl. No. 14/098,953, filed Dec. 6, 2013, Cunningham.
U.S. Appl. No. 14/100,237, filed Dec. 9, 2013, Reschke.
U.S. Appl. No. 14/103,971, filed Dec. 12, 2013, Roy.
U.S. Appl. No. 14/105,374, filed Dec. 13, 2013, Moua.
U.S. Appl. No. 14/109,459, filed Dec. 17, 2013, Hoarau.
U.S. Appl. No. 14/149,343, filed Jan. 7, 2014, Schmaltz.
U.S. Appl. No. 14/152,618, filed Jan. 10, 2014, Artale.
U.S. Appl. No. 14/152,690, filed Jan. 10, 2014, Hart.
U.S. Appl. No. 14/153,346, filed Jan. 13, 2014, Collings.
U.S. Appl. No. 14/162,192, filed Jan. 23, 2014, Garrison.
U.S. Appl. No. 14/164,569, filed Jan. 27, 2014, Heard.
U.S. Appl. No. 14/169,358, filed Jan. 31, 2014, Reschke.
U.S. Appl. No. 14/172,050, filed Feb. 4, 2014, Johnson.
U.S. Appl. No. 14/173,391, filed Feb. 5, 2014, Kharin.
U.S. Appl. No. 14/176,341, filed Feb. 10, 2014, Hart.
U.S. Appl. No. 14/176,684, filed Feb. 10, 2014, Chojin.
U.S. Appl. No. 14/177,812, filed Feb. 11, 2014, Dycus.
U.S. Appl. No. 14/178,540, filed Feb. 12, 2014, Anderson.
U.S. Appl. No. 14/182,894, filed Feb. 18, 2014, Hart.
U.S. Appl. No. 14/182,967, filed Feb. 18, 2014, Latimer.
U.S. Appl. No. 14/183,090, filed Feb. 18, 2014, Arts.
U.S. Appl. No. 14/188,935, filed Feb. 25, 2014, Reschke.
U.S. Appl. No. 14/196,066, filed Mar. 4, 2014, McCullough.
U.S. Appl. No. 14/204,770, filed Mar. 11, 2014, Dumbauld.

\* cited by examiner

DOUBLE-LENGTH JAW SYSTEM FOR ELECTROSURGICAL INSTRUMENT

CROSS REFERENCE TO RELATED APPLICATION

The present application claims the benefit of and priority to U.S. Provisional Application Ser. No. 61/664,492, filed on Jun. 26, 2012, the entire contents of which are incorporated herein by reference.

BACKGROUND

1. Technical Field

The following disclosure relates to an apparatus, system, and method for performing an electrosurgical procedure and, more particularly, to an apparatus, system and method that utilizes energy to seal and/or divide tissue.

2. Description of Related Art

Electrosurgical apparatuses (e.g., electrosurgical forceps) are well known in the medical arts and typically include a handle, a shaft, and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) or laparoscopic forceps for remotely accessing organs through smaller, puncture-like incisions. As a direct result thereof, patients tend to benefit from less scarring, fewer infections, shorter hospital stays, less pain, less restriction of activity, and reduced healing time. Typically, the forceps are inserted into the patient through one or more various types of cannulas or access ports (typically having an opening that ranges from about five millimeters to about twelve millimeters) that has been made with a trocar. As such, smaller cannulas are typically more desirable relative to larger cannulas. Forceps that are configured for use with small cannulas (e.g., cannulas less than five millimeters) may present design challenges for a manufacturer of electrosurgical instruments.

SUMMARY

According to one aspect of the present disclosure, an electrosurgical forceps is provided. The electrosurgical forceps includes a handle having a shaft extending therefrom defining a longitudinal axis. The handle is selectively movable to translate movement of the shaft along the longitudinal axis to actuate a pair of laterally spaced first and second jaw members pivotably connected to a distal end of the shaft. The first and second jaw members are moveable from an open position, wherein the first and second jaw members are in spaced relation relative to a stationary jaw member, to a closed position wherein the first and second jaw members cooperate with the stationary jaw member to grasp tissue therebetween. Each of the jaw members is adapted to connect to an electrosurgical energy source to conduct energy through tissue grasped therebetween to effect a tissue seal.

Alternatively or in addition, an inner shaft is axially disposed within the shaft and fixedly coupled to the stationary jaw member. The shaft may be configured to slide over the inner shaft upon movement along the longitudinal axis.

Alternatively or in addition, at least one of the first and second jaw members may be pivotally coupled to a distal end of the stationary jaw member.

Alternatively or in addition, movement of the shaft along the longitudinal axis may be configured to pivot the first and second jaw members substantially simultaneously between the open and closed positions.

Alternatively or in addition, distal movement of the shaft may be configured to actuate the jaw members to the closed position.

Alternatively or in addition, proximal movement of the shaft may be configured to actuate the jaw members to the open position.

Alternatively or in addition, the first and second jaw members may be disposed vertically offset from the stationary jaw member such that at least a portion of each of the first and second jaw members substantially aligns in vertical registration with at least a portion of the stationary jaw member when the jaw members are in the closed position.

Alternatively or in addition, an electrically conductive tissue sealing plate may be operatively coupled to each of the jaw members. The electrically conductive tissue sealing plates may be adapted to connect to the electrosurgical energy source to conduct energy through tissue grasped between the jaw members to effect the tissue seal.

Alternatively or in addition, the first and second jaw members may be disposed vertically offset from the stationary jaw member such that at least a portion of the electrically conductive tissue sealing plates of each of the first and second jaw members substantially aligns in vertical registration with at least a portion of the electrically conductive tissue sealing plate of the stationary jaw member when the jaw members are in the closed position.

Alternatively or in addition, at least one of the first and second jaw members may be generally L-shaped.

Alternatively or in addition, at least one of the first and second jaw members may be pivotally coupled to the shaft via a linkage. The linkage may be pivotally coupled to the shaft and configured to control a closing angle of the at least one jaw member relative to the stationary jaw member such that the at least one jaw member is disposed substantially parallel to the stationary jaw member when the jaw members are in the closed position.

According to a further aspect of the present disclosure, an electrosurgical forceps is provided. The electrosurgical forceps includes a handle having a shaft extending therefrom defining a longitudinal axis. The handle is selectively moveable to translate movement of the shaft along the longitudinal axis to actuate a pair of laterally spaced first and second jaw members pivotably connected to a distal end of the shaft. The first and second jaw members are moveable from an open position, wherein the first and second jaw members are in spaced relation relative to an opposing jaw member, to a closed position wherein the first and second jaw members cooperate with the opposing jaw member to grasp tissue therebetween. The first and second jaw members are vertically offset from the opposing jaw member such that at least a portion of each of the first and second jaw members substantially aligns in vertical registration with at least a portion of the opposing jaw member. Each of the jaw members is adapted to connect to an electrosurgical energy source to conduct energy through tissue grasped therebetween to effect a tissue seal.

Alternatively or in addition, proximal movement of the shaft may be configured to rotate the first jaw member counter clock-wise away from the opposing jaw member and the second jaw member clock-wise away from the opposing jaw member.

Alternatively or in addition, distal movement of the shaft may be configured to rotate the first jaw member clock-wise toward the opposing jaw member and the second jaw member counter clock-wise toward the opposing jaw member.

Alternatively or in addition, the opposing jaw member may be stationary.

Alternatively or in addition, an inner sleeve may be axially disposed within the shaft and fixedly coupled to the opposing jaw member. The shaft may be configured to slide over the inner shaft upon movement along the longitudinal axis.

Alternatively or in addition, the opposing jaw member may form a distal end of the inner sleeve.

According to a further aspect of the present disclosure, a method of performing an electrosurgical procedure is provided. The method includes the step of providing an electrosurgical forceps. The electrosurgical forceps includes a handle having a shaft extending therefrom defining a longitudinal axis. The handle is selectively movable to translate movement of the shaft along the longitudinal axis to actuate a pair of laterally spaced first and second jaw members pivotably connected to a distal end of the shaft. The first and second jaw members are moveable from an open position, wherein the first and second jaw members are in spaced relation relative to a stationary jaw member, to a closed position wherein the first and second jaw members cooperate with the stationary jaw member to grasp tissue therebetween. Each of the jaw members is adapted to connect to an electrosurgical energy source. The method also includes the steps of selectively moving the handle to translate movement of the shaft along the longitudinal axis to move the first and second jaw members from the open position to the closed position to grasp tissue therebetween and delivering electrosurgical energy from the electrosurgical energy source to each of the jaw members to effect a tissue seal.

Alternatively or in addition, the selectively moving step may include rotating the first jaw member clock-wise toward the stationary jaw member and the second jaw member counter clock-wise toward the stationary jaw member.

Alternatively or in addition, the first and second jaw members may be vertically offset from the stationary jaw member such that at least a portion of each of the first and second jaw members substantially aligns in vertical registration with at least a portion of the stationary jaw member.

BRIEF DESCRIPTION OF THE DRAWINGS

Various embodiments of the present disclosure are described hereinbelow with references to the drawings, wherein.

DETAILED DESCRIPTION

Detailed embodiments of the present disclosure are disclosed herein, however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use during catheter-based endoluminal procedures and/or for use with various access ports, including but not limited to those that are greater than and/or less than five millimeters. The present disclosure may be particularly advantageous for use with flexible-shafted instrument designs, such as catheter-based designs used in endoluminal procedures. With this purpose in mind, the present disclosure includes an electrosurgical forceps that includes jaw members associated with an end effector assembly of the electrosurgical forceps. The jaw members are operably coupled to an electrosurgical energy source and are each configured to conduct an electrical potential (e.g., positive or negative) therethrough that may be the same or opposite to that of the other jaw member(s) (e.g., in a bipolar configuration). In some embodiments, a shaft mechanically cooperates with a handle assembly and at least one of the jaw members to move the jaw members between an open configuration to a closed configuration. In the closed configuration, the jaw members utilize tissue grasped therebetween to form a closed loop electrical circuit such that a desired tissue effect (e.g., tissue seal) may be achieved.

Figure 1:
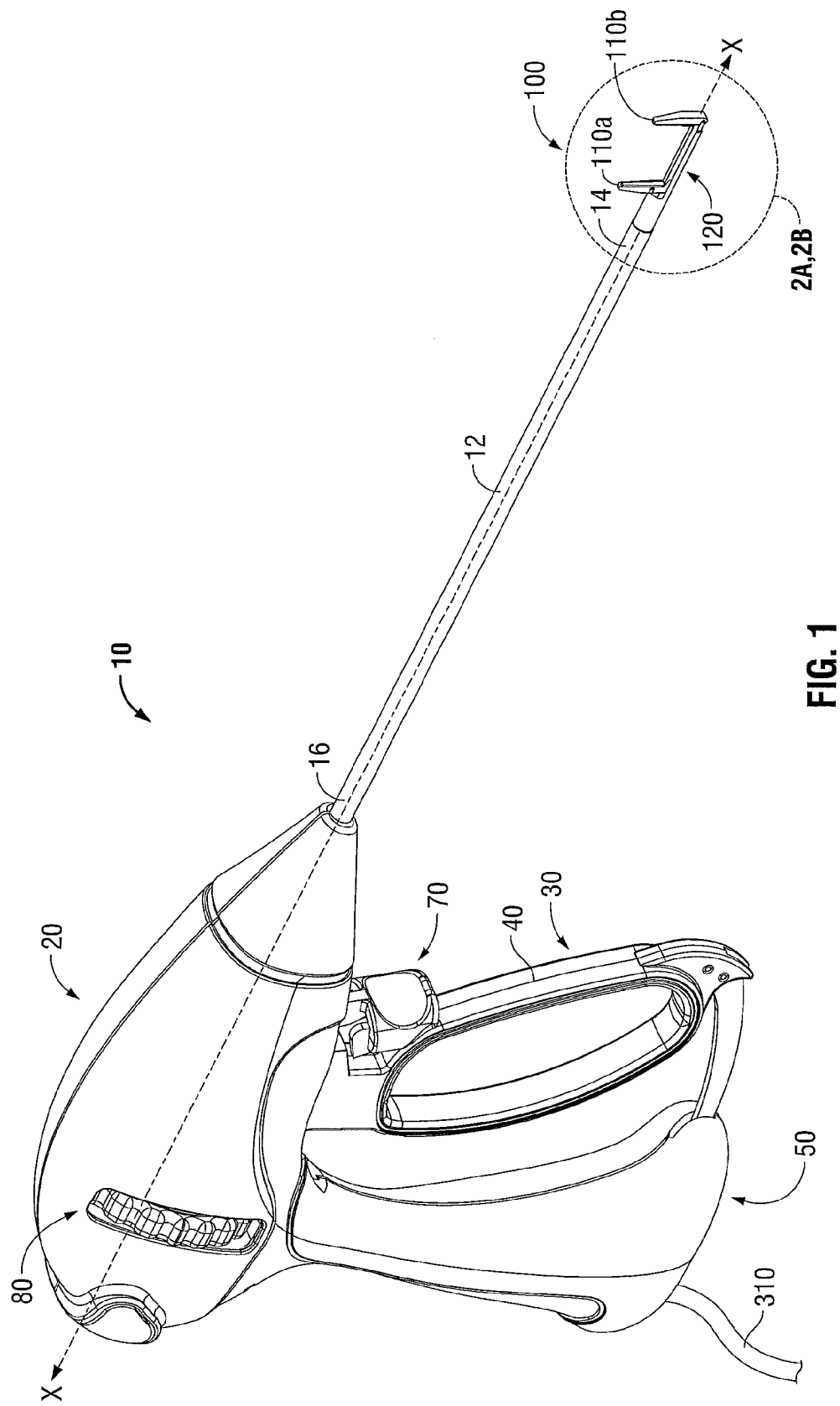
FIG. 1 is a perspective view of an endoscopic bipolar forceps showing a housing, a shaft, and an end effector assembly in accordance with an embodiment of the present disclosure.

Turning now to FIG. 1, an embodiment of an endoscopic bipolar forceps 10 is shown for use with various surgical procedures and generally includes a housing 20, a handle assembly 30, a rotating assembly 80, a trigger assembly 70, and an end effector assembly 100 that mutually cooperate to grasp, seal, and divide tubular vessels and vascular tissue. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that a version of the forceps for "open" procedures may also include the same or similar operating components and features as described below.

In the drawings and in the descriptions that follow, the term "proximal", as is traditional, will refer to the end of the forceps 10 that is closer to the user, while the term "distal" will refer to the end that is farther from the user.

Forceps 10 includes a shaft 12 that has a distal end 14 configured to mechanically engage the end effector assembly 100 and a proximal end 16 that mechanically engages the housing 20. Proximal end 16 of shaft 12 is received within housing 20 and appropriate mechanical and electrical connections relating thereto are established.

Forceps 10 includes an electrosurgical cable 310 that connects the forceps 10 to a source of electrosurgical energy, e.g., a generator (not shown). One such source of electrosurgical energy is described in commonly-owned U.S. Pat. No. 6,033, 399 entitled "ELECTROSURGICAL GENERATOR WITH ADAPTIVE POWER CONTROL". Cable 310 is internally divided into several cable leads (not shown) that each transmit electrical potentials through their respective feed paths through the forceps 10 to the end effector assembly 100.

For a more detailed description of handle assembly 30, movable handle 40, rotating assembly 80, and electrosurgical cable 310 (including line-feed configurations and/or connections) reference is made to commonly owned Patent Publication No. 2003/0229344, filed on Feb. 20, 2003, entitled VESSEL SEALER AND DIVIDER AND METHOD OF MANUFACTURING THE SAME.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable in either direction about a longitudinal axis "X-X" (See FIG. 1).

End effector assembly 100 is attached to the distal end 14 of shaft 12 and includes a pair of laterally spaced jaw members 110a and 110b that are configured to pivot relative to an opposing stationary jaw member 120. Movable handle 40 is operatively connected to shaft 12, which mechanically cooperate to impart movement of the jaw members 110a and 110b from an open position (FIG. 2A) wherein the jaw members 110a and 110b are disposed in spaced relation relative to the opposing stationary jaw member 120, to a clamping or closed position (FIG. 2B) wherein the jaw members 110a and 110b cooperate with stationary jaw member 120 to grasp tissue therebetween for sealing purposes. During movement of jaw members 110a, 110b from the open position to the closed position, jaw members 110a, 110b pivot toward each other, i.e., jaw member 110a pivots clock-wise toward stationary jaw member 120 and jaw member 110b pivots counter clockwise toward stationary jaw member 120. During movement of jaw members 110a, 110b from the closed position to the open position, jaw members 110a, 110b pivot away from each other, i.e., jaw member 110a pivots counter clock-wise away from stationary jaw member 120 and jaw member 110b pivots clock-wise away from stationary jaw member 120. With this purpose in mind, forceps 10 may include any suitable number of configurations, components, mechanical connections, and/or components (e.g., gears, links, springs, rods, etc.), and/or electro-mechanical connections, configurations, and/or components such that forceps 10 may function as intended.

In some embodiments, forceps 10 may be configured such that it is re-usable or such that it is fully or partially disposable depending upon a particular purpose or to achieve a particular result. For example, end effector assembly 100 may be selectively and releasably engageable with the distal end 14 of shaft 12 and/or the proximal end 16 of shaft 12 may be selectively and releasably engageable with the housing 20 and the handle assembly 30. In either of these two instances, the forceps 10 would be considered "partially disposable" or "reposable", e.g., a new or different end effector assembly 100 (or end effector assembly 100 and shaft 12) selectively replaces the old end effector assembly 100 as needed.

Figure 2A:
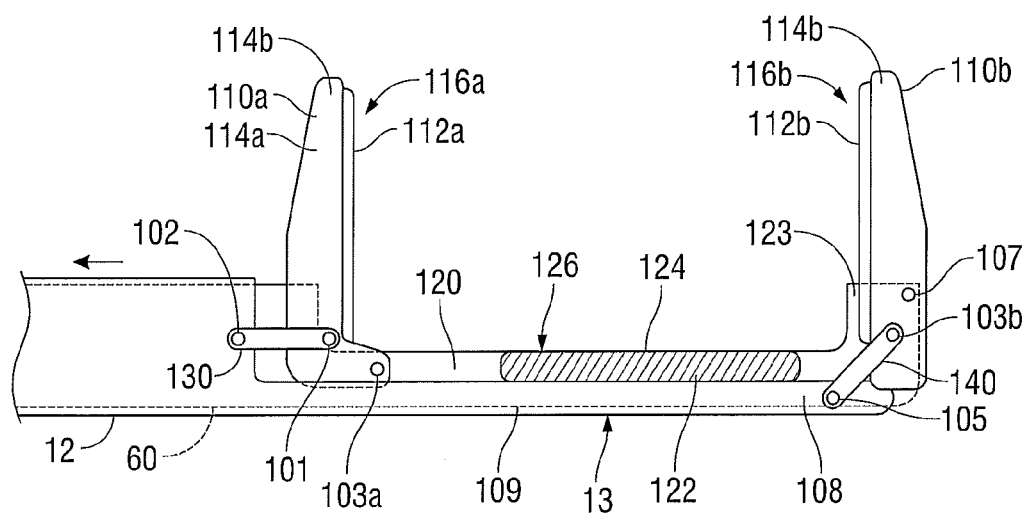
FIG. 2A is a schematic, side elevational view of the end effector assembly of FIG. 1 with the jaw members in open configuration.
Figure 2B:
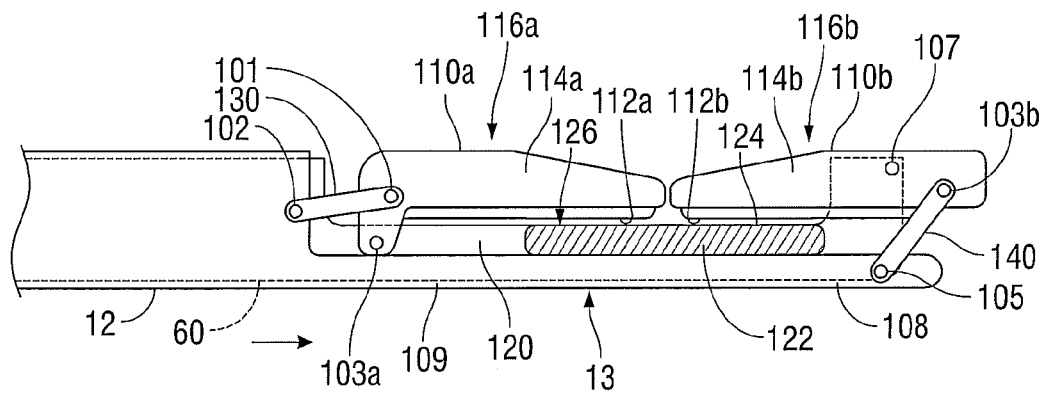
FIG. 2B is a schematic, side elevational view of the end effector assembly of FIG. 1 with the jaw members in a closed configuration.

As best shown in FIGS. 2A and 2B, jaw members 110a, 110b also include a jaw housing 116a, 116b, respectively, that has a respective insulative substrate or insulator 114a, 114b and an electrically conducive sealing surface 112a, 112b. Insulators 114a, 114b are configured to secure the electrically conductive sealing surfaces 112a, 112b, respectively, to respective jaw housings 116a, 116b. This may be accomplished by overmolding insulators 114a, 114b about jaw housings 116a, 116b, respectively, or by other suitable methods such as using adhesives.

Stationary jaw member 120 includes similar elements to jaw members 110a, 110b such as a jaw housing 126 having an insulator 124 and an electrically conductive sealing surface 122 that is secured to the jaw housing 126 by the insulator 124. This may be accomplished, for example, by overmolding insulator 124 about jaw housing 126, or by other suitable methods such as using adhesives.

The illustrated embodiment of FIGS. 2A and 2B is illustrative only in that any one or more of jaw members 110a, 110b or 120 may be configured to be devoid of an insulating substrate 114a, 114b or 124. For example, in some embodiments, jaw members 110a, 110b may include insulating substrate 114a, 114b, respectively, and stationary jaw member 120 may be configured such that insulating substrate 124 is removed and/or end effector assembly 100 may be manufactured such that stationary jaw member 120 does not include an insulating substrate. The insulators 114a, 114b, 124, electrically conductive sealing surfaces 112, 112b, 122, and the jaw housings 116, 126 are configured to limit and/or reduce many of the known undesirable effects related to tissue sealing, e.g., flashover, thermal spread, and stray current dissipation. In other embodiments, the jaw members 110a, 110b, and 120 may be manufactured from a ceramic-like material and the electrically conductive surfaces 112a, 112b, and 122 are coated onto the ceramic-like jaw members 110a, 110b, and 120, respectively.

The end effector assembly 100 may be designed as a unilateral assembly, i.e., stationary jaw member 120 is fixed relative to the shaft 12 and jaw members 110a and 110b pivot about respective pivot pins 103a and 103b relative to stationary jaw member 120 to grasp tissue, or as a bilateral assembly, i.e., jaw members 110a, 110b and stationary jaw member 120 pivot relative to each other to grasp tissue. In some embodiments and as will be discussed in further detail below, jaw members 110a, 110b are laterally spaced apart along a distally extended portion 13 of the distal end 14 of shaft 12 and are rotatable about pivot pins 103a and 103b, respectively, such that jaw members 110a, 110b pivot relative to stationary jaw member 120 for purposes of grasping tissue therebetween. In the illustrated embodiment of FIGS. 2A and 2B, jaw member 110b is generally linear in configuration and jaw member 110a is generally L-shaped.

With continued reference to FIGS. 2A and 2B, end effector assembly 100 includes one stationary jaw member 120 mounted in fixed relation to an inner shaft 60 that is coaxially disposed within the shaft 12. In some embodiments, stationary jaw member 120 is monolithically formed with inner shaft 60 such that stationary jaw member 120 forms a distal end of inner shaft 60. Jaw member 110b is pivotally coupled by way of pivot pin 103b to a linkage 140 that, in turn, couples to a distal end 108 of the extended portion 13 of shaft 12 via a pivot pin 105. Stationary jaw member 120 includes a generally L-shaped distal end 123 to which jaw member 110b is pivotally coupled via a pivot pin 107.

Jaw member 110a is pivotally coupled to a proximal portion of the stationary jaw member 120 via pivot pin 103a. As discussed above, jaw member 110a is generally L-shaped in the illustrated embodiment of FIGS. 2A and 2B. A linkage 130 is operably coupled by way of a pivot pin 101 to or substantially proximate to the vertex of the generally L-shaped jaw member 110a and, in turn, couples to the shaft 12 via a pivot pin 102 to effectively couple jaw member 110a to the shaft 12.

Shaft 12 is slidingly disposed about inner shaft 60 and is remotely operable by handle assembly 30 to translate movement of shaft 12 relative to inner shaft 60 along longitudinal axis "X-X". In order to open end effector assembly 100, shaft 12 is withdrawn or pulled in a proximal direction (see FIG. 2A), by actuating movable handle 40 relative to fixed handle 50. In order to close end effector assembly 100, shaft 12 is pushed or moved in a distal direction (see FIG. 2B), by actuating movable handle 40 relative to fixed handle 50. By way of example, moving shaft 12 in the proximal direction, as depicted in FIG. 2A, may be effected by squeezing movable handle 40 toward stationary handle 50. In this scenario, moving shaft 12 in the distal direction, as depicted in FIG. 2B, may be effected by approximating movable handle 40 away from stationary handle 50. In some embodiments, the configuration described in the above scenario may be reversed, e.g., squeezing movable handle 40 will move shaft 12 in the distal direction and approximating movable handle 40 away from stationary handle 50 will move shaft 12 in the proximal direction.

Jaw members 110a and 110b are actuated into the closed position by sliding the shaft 12 axially over inner shaft 60 in the distal direction such that jaw member 110a pivots about pivot pins 101 and 103a toward stationary jaw member 120 and jaw member 110b rotates about pivot pins 103b and 107 toward stationary jaw member 120, as depicted in FIG. 2B. In this manner, pushing shaft 12 distally closes jaw members 110a and 110b substantially simultaneously and, in conjunction with sealing surface 122, creates an effective tissue sealing area at least the size of tissue sealing surface 122. Counter clock-wise rotation of jaw member 110b about pivot pins 103b and 107 is aided by counter clock-wise rotation of linkage 140 about pivot pin 105 as shaft 12 is slid distally. More specifically, as linkage 140 rotates counter clock-wise about pivot pin 105, the angle of closure of jaw member 110b relative to stationary jaw member 120 is decreased so that as jaw member 110b moves into the closed position such that sealing surface 112b is disposed in a substantially parallel configuration relative to sealing surface 122, as depicted in FIG. 2B.

Jaw members 110a and 110b are actuated into the open position by sliding the shaft 12 axially over inner shaft 60 in the proximal direction such that jaw member 110a pivots about pivot pins 101 and 103a away from stationary jaw member 120 and jaw member 110b rotates about pivot pins 103b and 107 away from stationary jaw member 120, as depicted in FIG. 2B. In this manner, pulling shaft 12 proximally opens jaw members 110a and 110b substantially simultaneously. Clock-wise rotation of jaw member 110b about pivot pins 103b and 107 is aided by clock-wise rotation of linkage 140 about pivot pin 105 as shaft 12 is slid proximally.

As described above, the dual pivoting of jaw members 110a, 110b relative to stationary jaw member 120 operates to increase (e.g., double) the effective tissue sealing area between jaw members 110a, 110b and stationary jaw member 120. In some embodiments, sealing surfaces 112a and 112b may each be substantially half of the length of sealing surface 122 such that upon closure of jaw members 110a and 110b, sealing surfaces 112a, 112b are substantially equal to the length of sealing surface 122 to provide a relatively larger effective tissue sealing area with respect to a conventional pair of opposing tissue grasping jaw members. In this manner, stationary jaw member 120 may be manufactured with increased length relative to conventional jaw members to create a larger and/or longer effective tissue sealing surface relative to sealing surfaces of conventional surgical forceps.

As best shown in FIG. 2B, jaw members 110a and 110b are disposed generally adjacent to stationary jaw member 120 or are at least partially vertically offset from stationary jaw member 120. However, when jaw members 110a, 110b are in the closed position, as shown in FIG. 2B, at least a portion of jaw members 110a, 110b overlaps or substantially aligns in vertical registration with at least a portion of stationary jaw member 120. In some embodiments, tissue sealing surfaces 110a, 110b and 122 are disposed on respective jaw members 110a, 110b, and 120 in such a way so that when jaw members 110a, 110b are in the closed position, as shown in FIG. 2B, at least a portion of tissue sealing surfaces 112a and 112b overlaps or substantially aligns in vertical registration with tissue sealing surface 122 to form the effective tissue sealing surface area between jaw members 110a, 110b and stationary jaw member 120.

Figure 3A:
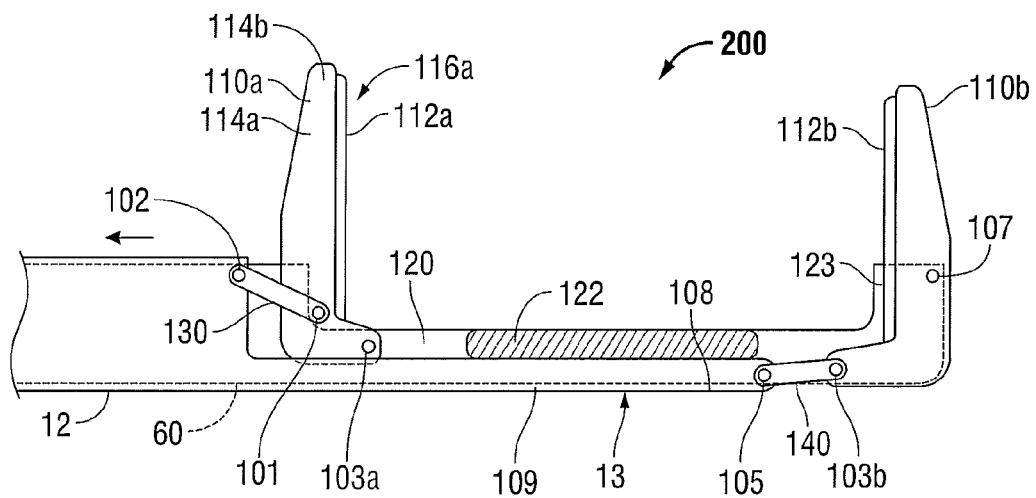
FIG. 3A is a schematic, side elevational view of an end effector assembly according to another embodiment of the present disclosure, with the jaw members in an open configuration.
Figure 3B:
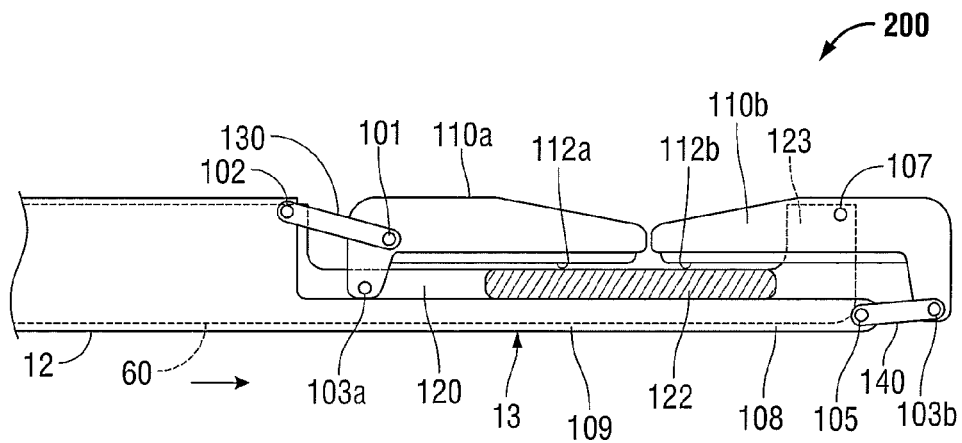
FIG. 3B is a schematic, side elevational view of the end effector assembly of FIG. 3A, with the jaw members in a closed configuration.

Turning now to FIGS. 3A and 3B, another embodiment of forceps 10 including an end effector assembly 200, in accordance with the present disclosure, is shown and described. End effector assembly 200 may include some, if not all, of the features and elements associated with end effector assembly 100 and as described above with reference to FIGS. 2A and 2B. End effector assembly 200 is substantially as described above with respect to end effector assembly 100 of FIGS. 1, 2A, and 2B and will only be described to the extent necessary to disclose the differences between the embodiments. While end effector assembly 200 is shown as having a unilateral jaw member arrangement, end effector assembly 200 may, in certain embodiments, have a bilateral jaw member arrangement.

As shown in FIGS. 3A and 3B, end effector assembly 200 includes opposing jaw members 110a and 110b having electrically conductive tissue sealing surfaces 112a and 112b, respectively. Jaw members 110a and 110b cooperate with stationary jaw member 120 to grasp tissue therebetween, as substantially described above with respect to the embodiment of FIGS. 2A and 2B. In the illustrated embodiment of FIGS. 2A and 2B, jaw member 110b is generally linear in configuration. The jaw member 110b shown in FIGS. 3A and 3B differs from jaw member 110b shown in FIGS. 2A and 2B in that the jaw member 110b of FIGS. 3A and 3B is generally L-shaped similar to jaw member 110a of FIGS. 2A and 2B.

With continued reference to FIGS. 3A and 3B, the generally L-shaped configuration of jaw member 110b causes the angle of closure of jaw member 110b relative to stationary jaw member 120 to increase such that jaw member 110b is permitted to rotate about pivot pins 103b and 107 toward stationary jaw member 120 so that sealing surface 112b is positioned substantially parallel to sealing surface 120 when jaw member 110b is in the closed position, as depicted in FIG. 3B.

In some embodiments, either or both of jaw members 110a and 110b may include a cam slot configuration (not shown) to facilitate actuation of jaw members 110a and 110b. In this scenario, for example, jaw member 110a may include a cam slot in which pivot pin 102 translates relative to the shaft 12 upon rotational movement of jaw member 110a about pivot pin 103a to improve the opening and closing motion of jaw member 110a. The location where pivot pin 102 couples to the shaft 12 may also be modified from the illustrated embodiments to improve the opening and closing motion of jaw member 110a. Likewise, jaw member 110b may include a cam slot in which pivot pin 105 and/or 103b translates upon rotational movement of jaw member 110b about pivot pin 107. In some embodiments, although not explicitly shown in the illustrated embodiments, the above described cam slot configuration may replace linkage 140 such that pivot pin 105 connects the distal end 108 of the extended portion 13 to jaw member 110*b* and translates within a cam slot upon rotational movement of jaw member 110*b*. The location where pivot pin 105 couples to the extended portion 13 may also be modified from the illustrated embodiments to improve the opening and closing motion of jaw member 110*b*.

Figure 4:
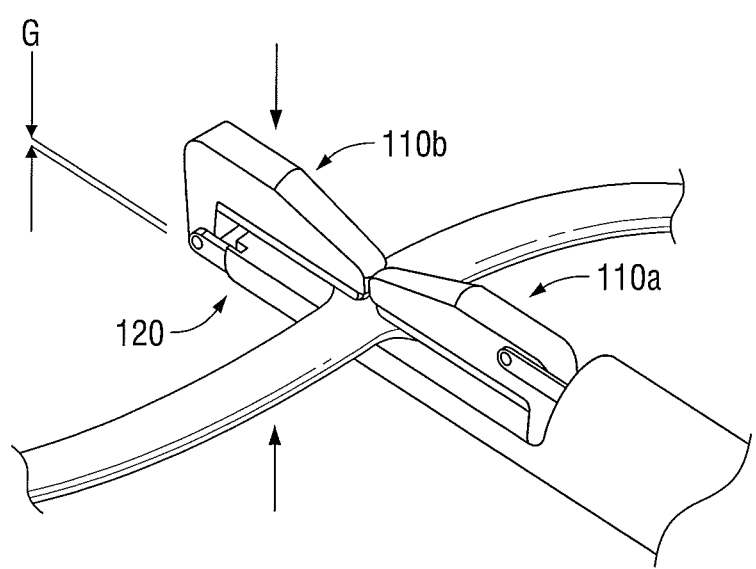
FIG. 4 is an enlarged, rear, perspective view of the end effector assembly of FIG. 1 shown grasping tissue.

FIG. 4 shows forceps 10 grasping tissue. As the handle 40 is squeezed, jaw members 110*a* and 110*b* are approximated toward stationary jaw member 120 to a clamped or closed position about tissue. Once jaws members 110*a* and 110*b* are fully compressed about the tissue, forceps 10 is now ready for selective application of electrosurgical energy and subsequent separation of the tissue. By controlling the intensity, frequency, and duration of the electrosurgical energy applied to tissue, the operator can either cauterize, coagulate/desiccate, seal, cut, and/or simply reduce or slow bleeding. Two mechanical factors play an important role in determining the resulting thickness of the sealed tissue and effectiveness of the seal, i.e., the pressure applied between opposing jaw members 110*a*, 110*b* and 120 and the gap distance "G" between the opposing sealing surfaces 112*a*, 112*b* and 122 of the jaw members 110*a*, 110*b* and 120 during the sealing process.

At least one jaw member (e.g., stationary jaw member 120) may include a stop member (not shown) extending a predetermined distance from the sealing surface 112*a*, 112*b*, or 122 that limits the movement of opposing jaw members 110*a*, 110*b* relative to stationary jaw member 120. The predetermined distance may be according to the specific material properties (e.g., compressive strength, thermal expansion, etc.) of the stop member(s) to yield a consistent and accurate gap distance "G" during sealing (FIG. 4). In some embodiments, the gap distance between opposing sealing surfaces 112*a*, 112*b* and 122 during sealing ranges from about 0.001 inches to about 0.006 inches and, in other embodiments, between about 0.002 and about 0.003 inches. Several suitable thermal spraying techniques may be utilized including, for example, depositing a broad range of heat resistant and insulative materials on various surfaces to create stop members for controlling the gap distance between electrically conductive surfaces 112*a*, 112*b* and 122.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
a handle having a shaft extending therefrom defining a longitudinal axis, the handle selectively movable to translate movement of the shaft along the longitudinal axis to actuate a pair of laterally spaced first and second jaw members pivotably connected to a distal end of the shaft and moveable from an open position, wherein the first and second jaw members are in spaced relation relative to a stationary jaw member, to a closed position wherein the first and second jaw members cooperate with the stationary jaw member to grasp tissue therebetween, each of the jaw members adapted to connect to an electrosurgical energy source to conduct energy through tissue grasped therebetween to effect a tissue seal.

2. An electrosurgical forceps according to claim 1, further comprising an inner shaft axially disposed within the shaft and fixedly coupled to the stationary jaw member, the shaft configured to slide over the inner shaft upon movement along the longitudinal axis.

3. An electrosurgical forceps according to claim 1, wherein at least one of the first and second jaw members is pivotally coupled to a distal end of the stationary jaw member.

4. An electrosurgical forceps according to claim 1, wherein movement of the shaft along the longitudinal axis is configured to pivot the first and second jaw members substantially simultaneously between the open and closed positions.

5. An electrosurgical forceps according to claim 1, wherein distal movement of the shaft is configured to actuate the jaw members to the closed position.

6. An electrosurgical forceps according to claim 1, wherein proximal movement of the shaft is configured to actuate the jaw members to the open position.

7. An electrosurgical forceps according to claim 1, wherein the first and second jaw members are disposed vertically offset from the stationary jaw member such that at least a portion of each of the first and second jaw members substantially aligns in vertical registration with at least a portion of the stationary jaw member when the jaw members are in the closed position.

8. An electrosurgical forceps according to claim 1, further comprising an electrically conductive tissue sealing plate operatively coupled to each of the jaw members, the electrically conductive tissue sealing plates adapted to connect to the electrosurgical energy source to conduct energy through tissue grasped between the jaw members to effect the tissue seal.

9. An electrosurgical forceps according to claim 8, wherein the first and second jaw members are disposed vertically offset from the stationary jaw member such that at least a portion of the electrically conductive tissue sealing plates of each of the first and second jaw members substantially aligns in vertical registration with at least a portion of the electrically conductive tissue sealing plate of the stationary jaw member when the jaw members are in the closed position.

10. An electrosurgical forceps according to claim 1, wherein at least one of the first and second jaw members is generally L-shaped.

11. An electrosurgical forceps according to claim 1, wherein at least one of the first and second jaw members is pivotally coupled to the shaft via a linkage, the linkage pivotally coupled to the shaft and configured to control a closing angle of the at least one jaw member relative to the stationary jaw member such that the at least one jaw member is disposed substantially parallel to the stationary jaw member when the jaw members are in the closed position.

12. An electrosurgical forceps, comprising:
a handle having a shaft extending therefrom defining a longitudinal axis, the handle selectively movable to translate movement of the shaft along the longitudinal axis to actuate a pair of laterally spaced first and second jaw members pivotably connected to a distal end of the shaft and moveable from an open position, wherein the first and second jaw members are in spaced relation relative to an opposing jaw member, to a closed position wherein the first and second jaw members cooperate with the opposing jaw member to grasp tissue therebetween, the first and second jaw members vertically offset from the opposing jaw member such that at least a portion of each of the first and second jaw members substantially aligns in vertical registration with at least a portion of the opposing jaw member, each of the jaw members adapted to connect to an electrosurgical energy source to conduct energy through tissue grasped therebetween to effect a tissue seal.

13. An electrosurgical forceps according to claim 12, wherein proximal movement of the shaft is configured to rotate the first jaw member counter clock-wise away from the opposing jaw member and the second jaw member clock-wise away from the opposing jaw member.

14. An electrosurgical forceps according to claim 12, wherein distal movement of the shaft is configured to rotate the first jaw member clock-wise toward the opposing jaw member and the second jaw member counter clock-wise toward the opposing jaw member.

15. An electrosurgical forceps according to claim 12, wherein the opposing jaw member is stationary.

16. An electrosurgical forceps according to claim 12, further comprising an inner sleeve axially disposed within the shaft and fixedly coupled to the opposing jaw member, the shaft configured to slide over the inner shaft upon movement along the longitudinal axis.

17. An electrosurgical forceps according to claim 16, wherein the opposing jaw member forms a distal end of the inner sleeve.

18. A method of performing an electrosurgical procedure, the steps comprising:
   providing an electrosurgical forceps, including:
      a handle having a shaft extending therefrom defining a longitudinal axis, the handle selectively movable to translate movement of the shaft along the longitudinal axis to actuate a pair of laterally spaced first and second jaw members pivotably connected to a distal end of the shaft and moveable from an open position, wherein the first and second jaw members are in spaced relation relative to a stationary jaw member, to a closed position wherein the first and second jaw members cooperate with the stationary jaw member to grasp tissue therebetween, each of the jaw members adapted to connect to an electrosurgical energy source;
   selectively moving the handle to translate movement of the shaft along the longitudinal axis to actuate the first and second jaw members from the open position to the closed position to grasp tissue therebetween; and
   delivering electrosurgical energy from the electrosurgical energy source to each of the jaw members to effect a tissue seal.

19. A method according to claim 18, wherein the selectively moving step includes rotating the first jaw member clock-wise toward the stationary jaw member and the second jaw member counter clock-wise toward the stationary jaw member.

20. A method according to claim 18, wherein the first and second jaw members are vertically offset from the stationary jaw member such that at least a portion of each of the first and second jaw members substantially aligns in vertical registration with at least a portion of the stationary jaw member.

* * * * *